(12) United States Patent
Tanaka et al.

(10) Patent No.: US 7,285,790 B2
(45) Date of Patent: Oct. 23, 2007

(54) OPTICAL MEASUREMENT SYSTEM FOR LIVING BODIES AND METHOD THEREOF

(75) Inventors: Naoki Tanaka, Tokyo (JP); Takusige Katura, Hatoyama (JP); Masashi Kiguchi, Kawagoe (JP); Hiroki Sato, Oi (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 336 days.

(21) Appl. No.: 11/044,040

(22) Filed: Jan. 28, 2005

(65) Prior Publication Data

US 2006/0006343 A1    Jan. 12, 2006

(30) Foreign Application Priority Data

Jul. 8, 2004    (JP) ............................. 2004-201608

(51) Int. Cl.
*A61B 5/00*    (2006.01)
(52) U.S. Cl. .................. 250/458.1; 356/342; 356/340
(58) Field of Classification Search ............. 250/458.1; 356/342, 340
See application file for complete search history.

(56) References Cited

U.S. PATENT DOCUMENTS

| | | | |
|---|---|---|---|
| 4,058,113 A | 11/1977 | Fields | |
| 5,331,969 A | 7/1994 | Silberstein | |
| 7,022,083 B2 * | 4/2006 | Tanaka et al. | 600/504 |

FOREIGN PATENT DOCUMENTS

| | | |
|---|---|---|
| EP | 0 541 315 | 5/1993 |
| JP | H09-098972 A | 4/1997 |
| JP | 2000-237194 A | 9/2000 |
| JP | 2004-237194 | 9/2000 |
| JP | 2003-79626 | 3/2003 |
| WO | WO 02-032317 A | 4/2002 |

OTHER PUBLICATIONS

Physical Review Letters, vol. 81, No. 15, Oct. 12, 1998 P. Tass et al.

* cited by examiner

*Primary Examiner*—Constantine Hannaher
*Assistant Examiner*—Djura Malevic
(74) *Attorney, Agent, or Firm*—Antonelli, Terry, Stout & Kraus, LLP.

(57) ABSTRACT

A response period is determined arbitrarily. A satisfactory detecting ability may not be provided because of an artifact or the like contained in a signal. Therefore, an effective detection method and an effective display method of presenting results of detection must be developed. A series of tasks (stimuli) or a selected measurement signal is used as a reference signal, and a phase difference of any other measurement signal from the reference signal is calculated. The synchronousness of the phase of the measurement signal with the phase of the reference signal is numerically expressed. The thus obtained numerical value is statistically processed in order to numerically express a degree of reliability. Thus, a brain activity or a functional connectivity is visualized.

7 Claims, 10 Drawing Sheets

|  | AMPLITUDE SYNCHRONOUSNESS | PHASE SYNCHRONOUSNESS |
|---|---|---|
| SIGNAL EXAMPLE A | O | O |
| SIGNAL EXAMPLE B | X | O |

FIG.4A
| D | 1 | S | 2 | D | 3 | S |
|---|---|---|---|---|---|---|
| 4 | D | 5 | S | 6 | D | 7 |
| S | 8 | D | 9 | S | 10 | D |
| 11 | S | 12 | D | 13 | S | 14 |
| D | 15 | S | 16 | D | 17 | S |
| 18 | D | 19 | S | 20 | D | 21 |
| S | 22 | D | 23 | S | 24 | D |
FIG.4B
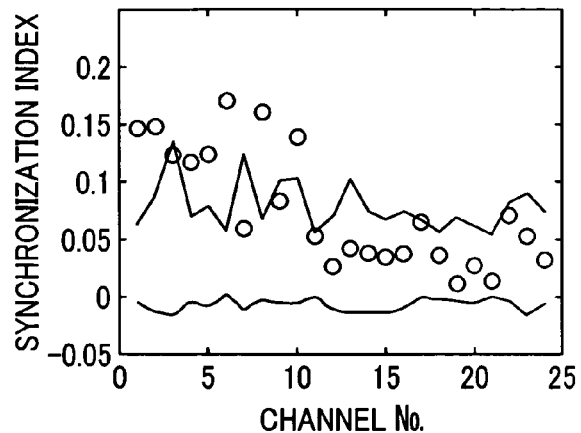
FIG.4C
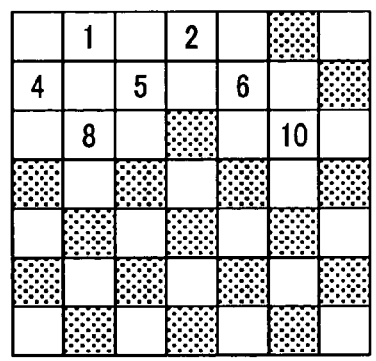
FIG.4D
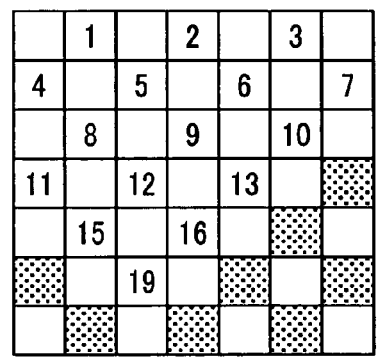
FIG.4E
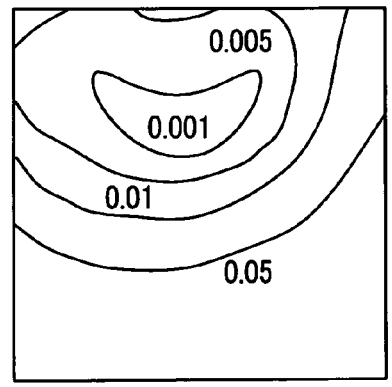
FIG.4F
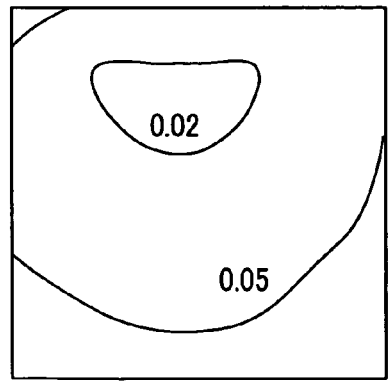

FIG.6

CHANNELS HIGHLY PHASE-
SYNCHRONIZED WITH STANDARD SIGNAL
(PLAYBACK SIGNAL)

IN DESCENDING ORDER OF
PHASE SYNCHRONIZATION INDEX :

1. PROBE 2  Ch 10
2. PROBE 2  Ch 5
3. PROBE 3  Ch 9
4. PROBE 4  Ch 5
5. PROBE 3  Ch 5
6. PROBE 4  Ch 4
7. PROBE 1  Ch 6
8. PROBE 2  Ch 12
9. PROBE 3  Ch 11
10. PROBE 1  Ch 10

S1

S2

S3

S4

WHOLE IMAGE

OPTICAL MEASUREMENT SYSTEM FOR LIVING BODIES AND METHOD THEREOF

CLAIM OF PRIORITY

The present invention claims priority from Japanese application JP 2004-201608 filed on Jul. 8, 2004, the content of which is hereby incorporated by reference into this application.

BACKGROUND OF THE INVENTION

1. Field of the Invention

The present invention relates to the field of measurement of a brain function disclosed in, for example, Japanese Patent Laid-Open No. 2000-237194.

2. Description of the Related Art

An example of measurement of a brain function will be described in conjunction with FIG. 1A and FIG. 1B. FIG. 1A shows the configuration of a brain function measurement system and the relationship thereof to a subject. FIG. 1B shows an example of the distribution of positions S at which a light irradiating means for irradiating the subject's head with light is located, and positions D at which a receiving optical fiber for receiving light that has been applied to the subject's head and transmitted thereby is located.

The brain function measurement system includes: a plurality of light sources 102a to 102d that generates light waves having difference wavelengths (the light sources 102a and 102c generate light having a wavelength of, for example, 780 nm, and the light sources 102b and 102d generate light having a wavelength of, for example, 830 nm); oscillators 101a and 101b and oscillators 101c and 101d that modulate at different frequencies the intensities of light waves emitted from the plurality of light sources 102a and 102b or light sources 102c and 102d; a plurality of light irradiating means for irradiating, which a coupler 104a produces using the intensity-modulated light waves having propagated along optical fibers 103a and 103b, and light, which a coupler 104b produces using the intensity-modulated light waves having propagated along optical fibers 103c and 103d, different positions on the head skin of a subject 106 with light over light irradiating optical fibers 105a and 105b; and a plurality of pieces of light receiving means composed of a plurality of receiving optical fibers 107a to 107f, which is disposed so that the ends thereof will be located equidistantly from (for example, 30 mm away from) the light-applied positions, that is, the plurality of pieces of light irradiating means, and light receivers 108a to 108f disposed at the other ends of the optical fibers 107a to 107f.

In the example of FIG. 1A, the three receiving optical fibers (D in the drawing) 107a to 107c and three receiving optical fibers 107d to 107f are, as shown in FIG. 1B, disposed around the light irradiating optical fibers (S in the drawing) 105a and 105b, so that light waves transmitted by a living body will be converged on the optical fibers and detected. The detected light waves transmitted by the living body are photoelectrically converted by the light receivers 108a to 108f. The light receiving means detects light, which is transmitted by the subject's intracranial regions while being reflected therefrom, and converts the light into an electrical signal. The light receivers 108a to 108f are realized with photoelectric conversion elements such as photoelectric multipliers or photodiodes.

Electrical signals that represent the intensities of light waves transmitted by a living body and that result from photoelectric conversion performed by the light receivers 108a to 108f (hereinafter, living body-transmitted light intensity signals) are transferred to lock-in amplifiers 109a to 109h. The light receivers 108c and 108d detect the intensities of living body-transmitted light waves converged on the receiving optical fibers 107c and 107d that are located equidistantly from the light irradiating optical fibers 105a and 105b respectively. The signals proportional to the light intensities detected by the light receivers 108c and 108d are each separated into two portions and transferred to the lock-in amplifiers 109c and 109e or the lock-in amplifiers 109d and 109f. Signals that are the outputs of the oscillators 101a and 10b as well as 101c and 101d modulated in intensity at intensity modulation frequencies are transferred as signals of reference frequencies to the lock-in amplifiers 109a to 109d, and 109e to 109h respectively. Consequently, the living body-transmitted light intensity signals representing the intensities of light waves emitted from the light sources 102a and 102b are separated from each other and transmitted from the lock-in amplifiers 109a to 109d. The living body-transmitted light intensity signals representing the intensities of light waves emitted from the light sources 102c and 102d are separated from each other and transmitted from the lock-in amplifiers 109e to 109h.

The transmitted light intensity signals separated from one another in units of a wavelength and transmitted from the lock-in amplifiers 109a to 109h are analog-to-digital converted by an analog-to-digital converter (hereinafter, an A/D converter) 110, and then transferred to a measurement control computer 111. The measurement control computer 111 uses each of the transmitted-light intensity signals, that is, detection signals produced at detected positions to thus arithmetically or logically calculate relative changes in an oxyhemoglobin concentration, a deoxy-hemoglobin concentration, and a total hemoglobin concentration. The relative changes are stored as time-sequential information on each of the measured positions in a storage device included in the computer 111. Herein, the change in the total hemoglobin concentration is calculated as the sum of the changes in the oxyhemoglobin concentration and deoxy-hemoglobin concentration.

On the other hand, in order to measure a brain function of a subject, a predetermined stimulus or task is applied to the subject and the subject's response to the stimulus or task is assessed. A centralized control/data processing/result display computer 114 issues a command to the measurement control computer 111. The measurement control computer 111 in turn uses a stimulus/task command presentation device 113 to apply a stimulus/task instruction to the subject according to a prepared stimulus/task instruction sequence. A response to the stimulus/task instruction made by the subject's brain is optically measured as described above. The centralized control/data processing/results display computer 114 and the measurement control computer 111 communicate required information to each other.

Conventionally, in order to assess a subject's response to a stimulus or task, the significance of a signal representing an average response obtained as a result of repetitive measurements is tested based on the amplitude of the signal. A significantly active area is then identified (refer to Japanese Unexamined Patent Application Publication No. 2000-237194).

SUMMARY OF THE INVENTION

A response period is determined arbitrarily. Moreover, a satisfactory detecting capability may not be provided because of an artifact or the like contained in a signal. Therefore, an effective detection method capable of accurately assessing a subject's response to a stimulus or task and a display method for presenting the results of detection are requested to be developed.

The present invention is based on the principle that activities of the same source are in phase with one another. For assessment of a subject's response, an active area is detected by checking if the phase of a stimulus or task applied to the subject is synchronous with the phase of the subject's response. The synchronousness is analyzed by checking the amplitudes and phases of both the signals. FIG. 2A and FIG. 2B are schematic explanatory diagrams concerning the synchronousness of a signal with a task. FIG. 2A shows signal examples A and B resulting from application of a task to a subject during a task period that comes cyclically and alternately with a rest period. The signal example A is synchronous with the task in both the amplitude and phase thereof. The signal example B is synchronous with the task in the phase thereof but asynchronous therewith in the amplitude thereof. FIG. 2B is a table listing whether the amplitudes and phases of the signal examples are synchronous with the amplitude and phase of the task.

The present invention takes account of the fact that the synchronousness of the amplitude of a signal with that of a task is unacceptable as a condition under which a subject's response is assessed. Namely, a signal representing a stimulus or task applied to a subject is used as a reference signal, and a phase difference of a measurement signal representing the subject's response from the reference signal is calculated. The synchronousness of the phase of the measurement signal with the reference signal is numerically expressed. The numerical value is statistically processed in order to thus numerically express a degree of reliability. A brain activity or a functional connectivity is visualized based on significant data.

BRIEF DESCRIPTION OF THE DRAWINGS

FIG. 2A shows signal examples A and B produced responsively to a task applied during a task period that comes cyclically and alternately with a rest period;

FIG. 2B is a table listing whether the amplitudes and phases of the signal examples A and B are synchronous with the task;

FIG. 4A to FIG. 4F are explanatory diagrams concerning an example of the results of analysis of the synchronousness of the phase of a signal performed according to the first embodiment;

FIG. 4A shows an example of the structure of a probe;

FIG. 4B graphically shows the results of assessment of the synchronousness of the phase of a signal on the basis of the results of measurement of a change in a total hemoglobin content;

FIG. 4C shows the results shown in FIG. 4B and displayed in a different form;

FIG. 4D shows, for comparison, the results of a test, which is performed as conventionally on the same results of measurement in order to check the synchronousness of the amplitude of a signal produced during stimulation, displayed in the same form as FIG. 4C;

FIG. 4E shows an example of a display form in which the results shown in FIG. 4B and FIG. 4C are presented to a user in an easier-to-understand manner;

FIG. 4F shows an example of an image displayed in order to present the results shown in FIG. 4D in the same manner as the results shown in FIG. 4C;

FIG. 6 shows measurement channels in which signals which are produced responsively to hearing of a played-back signal serving as a standard signal and whose phases are highly synchronous with the phase of the standard signal;

DESCRIPTION OF THE PREFERRED EMBODIMENTS

Figure 1A:
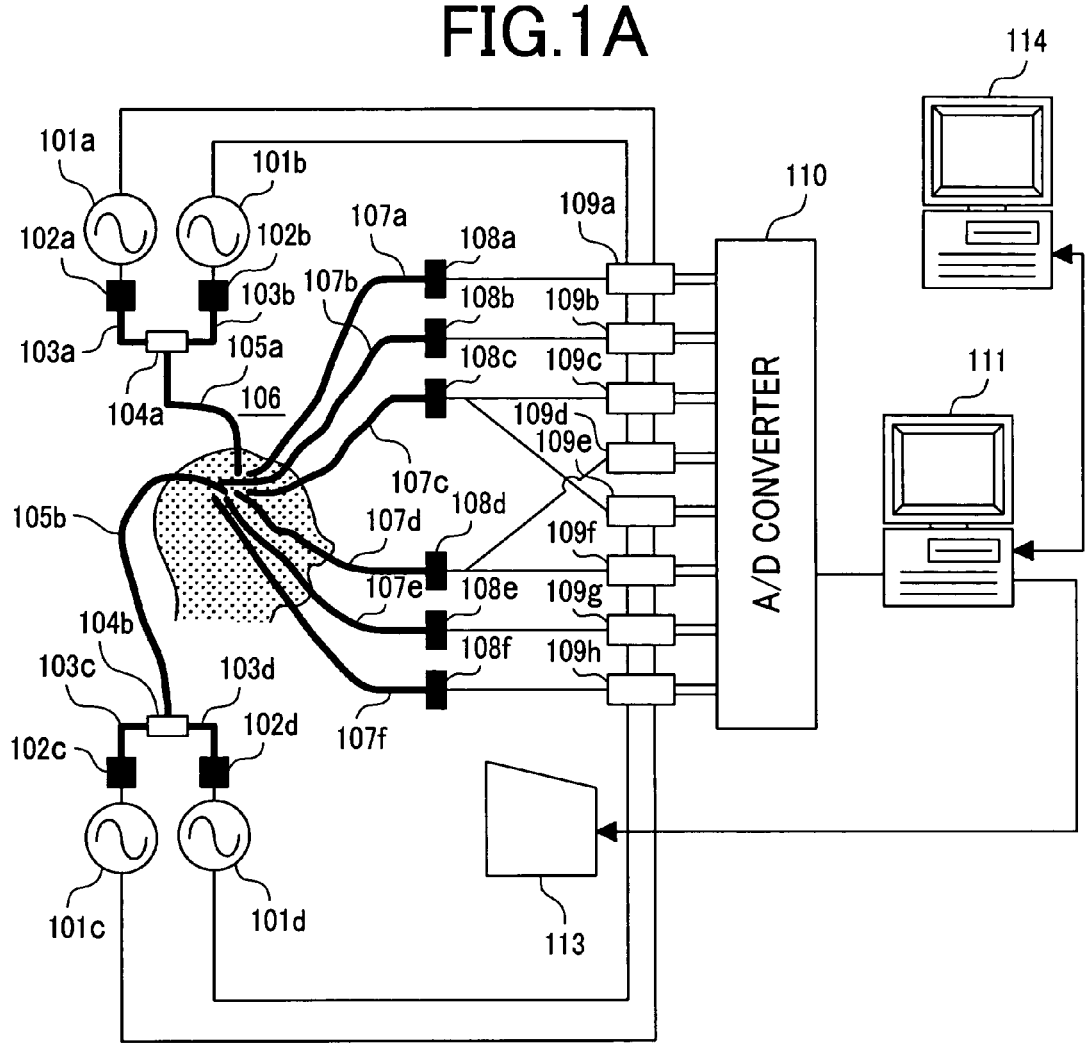
FIG. 1A shows the configuration of a brain function measurement system and the relationship of the system to a subject.

With consideration taken into the fact that when a signal produced responsively to a stimulus or task is synchronous with a signal representing the stimulus or task, the phase difference between the signals is fixed, how long the phase difference is fixed is discussed using actual data.

For calculation of a phase difference, the Hilbert transformation is used to obtain instantaneous phases of signals. A phase difference observed at each time instant is calculated from the instantaneous phases.

The Hilbert transformation will be described. A Hilbert transform $g(t)$ of a real variable function $f(t)$ and an inverse Hilbert transform thereof are provided as formulae (1) and (2) below.

$$g(t) = f(t) \otimes \frac{1}{\pi t} = \frac{1}{\pi} \int_{-\infty}^{\infty} \frac{f(\tau)}{t - \tau} d\tau \qquad (1)$$

-continued $$f(t) = g(t) \otimes \frac{1}{\pi t} = \frac{-1}{\pi} \int_{-\infty}^{\infty} \frac{g(\tau)}{t-\tau} d\tau \quad (2)$$

where ⊗ denotes convolution.

A measurement signal is regarded as the real variable function f(t), and an analysis signal Z(t) is defined as follows:

$$Z(t)=f(t)+jg(t) \quad (3)$$

When the formula (3) is defined in the system of polar coordinates, the following formula (4) is drawn out:

$$Z(t)=r(t)e^{j\theta(t)} \quad (4)$$

By rewriting the formula (4), the following formulae (5) and (6) are drawn out:

$$r(t) = \sqrt{f(t)^2 + g(t)^2} \quad (5)$$

$$\theta(t) = \tan^{-1} \frac{g(t)}{f(t)} \quad (6)$$

where r(t) denotes the instantaneous amplitude of the measurement signal f(t), and θ(t) denotes the instantaneous phase thereof.

According to an exemplary algorithm, the analysis signal Z(t) is obtained as a one-side Fourier transform of the measurement signal f(t). Namely, negative-frequency components of a signal are assigned 0. The measurement signal f(t) is fast-Fourier-transformed in order to approximate the analysis signal to the measurement signal. Coefficients expressing fast-Fourier-transformed negative-frequency components are replaced with zeros. The results are inverse-fast-Fourier-transformed in order to obtain the analysis signal Z(t).

To be more specific, an algorithm having four steps described below is employed. The number of input data items shall be n.

At the first step, input data is fast-Fourier-transformed, and the resultant data is represented with a vector y.

At the second step, a vector h causing h(i) to assume a value described below is produced. Namely, when i assumes 1 or (n/2)+1, h(i) will be 1. When i assumes 2, 3, etc., or (n/2), h(i) will be 2. When i assumes (n/2)+2, etc., or n, h(i) will be 0.

At the third step, the product of the vectors y and h is calculated for each h(i).

At the fourth step, an inverse fast-Fourier transform of a data stream calculated at the third step is worked out. The first n elements of the resultant data are provided as the analysis signal Z(t).

Statistical discussion is made in order to objectively verify how long a phase difference is fixed. The distribution of phase differences is expressed in the form of a histogram having Nb bins and covering a range from −π to π. A synchronization index (SI) is adopted as a statistical index and defined as a formula (7) below.

$$SI = \frac{S_{random} - S}{S_{random}} \quad (7)$$

By rewriting the formula (7), formulae (8) and (9) are drawn out as follows:

$$S = -\sum_{i=1}^{Nb} p_i \log_2 p_i \quad (8)$$

$$S_{random} = \log_2 Nb \quad (9)$$

where pi denotes a probability density function of a random variable represented by the i-th bin.

In the formula (8), pi denotes the probability of a phase difference represented by the i-th bin.

If the distribution of phase differences is fully uniform, that is, if the phase of a signal is not at all synchronous, $S=S_{random}$ becomes true. SI is therefore 0. If the phase of a signal is fully synchronous, SI is 1. Since actual measurement data contains various kinds of noises, a clear-cut result such as SI=1 or 0 is very rare. If SI assumes an intermediate value, whether the phase of a signal is synchronous is verified statistically.

As a technique of verifying whether the phase of a signal is synchronous, a surrogate data method is employed. The surrogate data method is a framework for performing a test of hypothesis described below.

1. Numerous data items having an accurate statistical property are produced from original data (using random numbers).

2. An index to be assigned to random data is calculated.

3. The index assigned to the original data is tested based on sample values selected from among numerous indices.

As surrogate data, data subjected to the same filtering as a signal concerned during random sampling is adopted. If the distribution of synchronization indices (SI), that is, statistical indices calculated from 50 surrogate data items is a normal distribution (average: 0.2236, standard deviation: 0.0219), a synchronization index larger than 0.2800 may be adopted as a threshold for verification at a significance level of 1%. Furthermore, in order to discuss a time-sequential change in a synchronous state, a short time window (covering several hundreds of data items) may be designated. In this case, a synchronization index serving as a statistical index is calculated during the period, and a synchronization index calculated at a center time instant within the time window is adopted as a representative synchronization index. The time window is shifted in units of a certain time in order to calculate a time-sequential change in the synchronization index.

First Embodiment

Figure 1B:
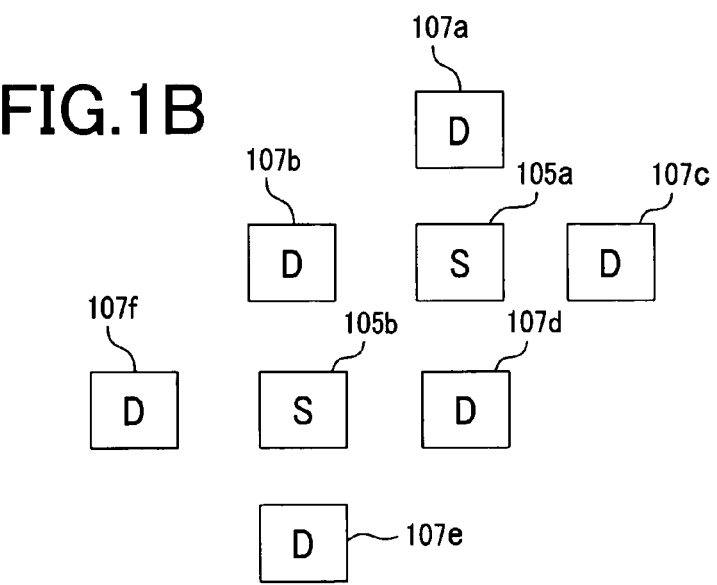
FIG. 1B shows an example of the distribution of positions S at which a light irradiating means for irradiating a subject's head with light is located, and positions D at which a receiving optical fiber for receiving light applied to the subject's head and transmitted thereby is located.
Figure 3:
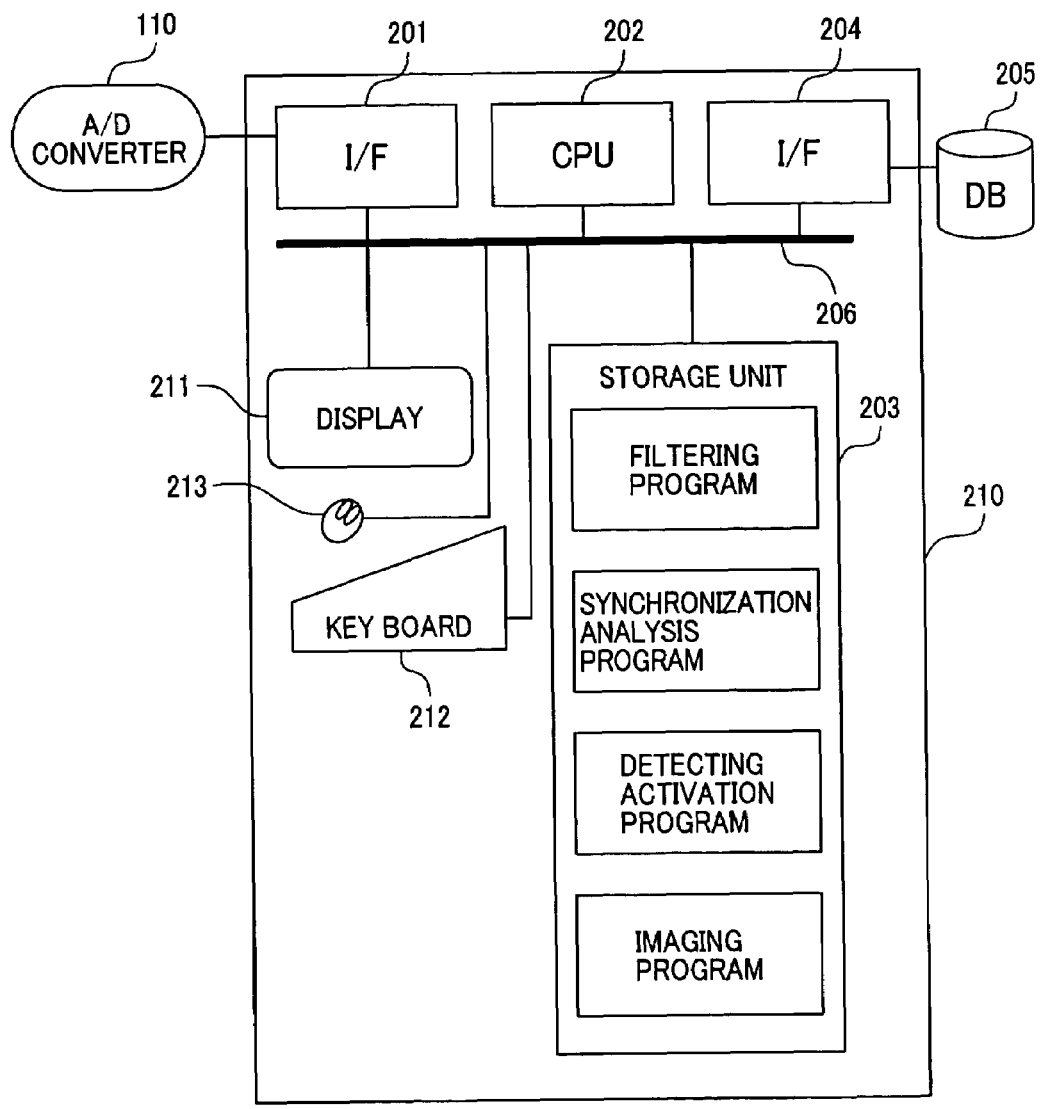
FIG. 3 is a block diagram showing the configuration of a living body measurement system in accordance with the first embodiment.

FIG. 3 is a block diagram showing the configuration of a living body measurement system in accordance with the first embodiment. The living body measurement system 210 corresponds to a measuring facility of the measurement control computer 111 shown in FIG. 1. The living body measurement system includes an interface 201 that provides the interface with the A/D converter 110, a CPU 202 that performs a series of actions, a storage unit 203 in which programs and data are stored, an interface 204 that provides the interface with external equipment 205, and a bus 206 over which these components are interconnected. Moreover, a display means 211, a keyboard 212, and a pointing device (for example, a mouse) 213 are connected on the bus, and used to present the results of analysis to an operator of the measurement control computer 111. Moreover, the operator uses the display means 211, keyboard 212, and pointing device to enter data. Herein, the programs stored in the storage unit 203 include a filtering program that performs required filtering on a signal, a phase synchronousness analyzing program for analyzing the synchronousness of the phase of each of a group of filtered signals or of an extraneous signal, an activity detecting program for detecting a neural activity from the results of analysis performed on the synchronousness of a phase, and an imaging program for presenting a user the detected neural activity in an easy-to-understand manner. The results of detection are displayed on the display means 211. The programs preserved in the storage unit 203 are interpreted and run by a central processing unit 202.

FIG. 4A to FIG. 4F are explanatory diagrams showing examples of the results of analysis performed on the synchronousness of a phase according to the first embodiment.

FIG. 4A shows an example of the structure of a probe. The probe is placed on a subject's head, and has a light irradiating optical fiber S and a receiving optical fiber D arranged alternately so that measurement channels 1 to 24 will be formed among the light irradiating optical fibers S and receiving optical fibers D. Thus, the probe measures a change in a total hemoglobin content caused by a visual stimulus. The numbers of light irradiating optical fibers S and receiving optical fibers D included in the probe can be determined arbitrarily in consideration of a position at which the probe is placed or the size of the subject's head. The visual stimulus to be applied to the subject is a checkerboard having a size of 16 by 16 and having red and black squares. A frequency at which the red and black squares are switched is set to 8 Hz. A rest period is set to 20 sec, and a stimulus (task) period is set to 18 sec. This test is repeated six times.

FIG. 4B shows the results of assessment on the synchronousness of a phase performed by measuring a change in a total hemoglobin content. The axis of abscissas indicates channel numbers, and the axis of ordinates indicates synchronization indices detected in the respective channels. An average of six synchronization indices obtained by repeating the test six times is indicated with a circle. Moreover, a broken line is drawn in order to indicate a statistical reference value (at a significance level of 1%). Consequently, in this example, a signal that can be assessed to be synchronous with the stimulus of the checkerboard is detected in channels 1, 2, 4, 5, 6, 8, and 10.

FIG. 4C shows the results shown in FIG. 4B in a different manner. The channel numbers of the channels 1, 2, 4, 5, 6, 8, and 10 in which a signal assessed to be significant at the significance level of 1% is produced are displayed, and squares indicating channels in which an insignificant signal is produced are filled with black dots. The positions of the measuring fibers are indicated with blank squares. FIG. 4C demonstrates that the brain activity is observed at a position on the head associated with the upper part of the probe.

FIG. 4D shows in the same manner as FIG. 4C, for the purpose of comparison, the results of a test of hypothesis performed based on the synchronous of the amplitude of a signal that is assessed during stimulation as conventionally by measuring a change in a total hemoglobin content. In the test of hypothesis based on the synchronousness of the amplitude of a signal, a brain activity cannot be detected with a significance level set to 1%. The significance level is therefore set to 5%. Compared with FIG. 4C, FIG. 4D demonstrates that the brain activity is observed at a position on the head associated with the majority of the probe. This signifies that the present invention exhibits higher sensitivity and detects the localized brain activity.

FIG. 4E shows an example of a display form in which the results of FIG. 4B or FIG. 4C are presented to a user in an easier-to-understand manner. Significance levels at which the results of detection are assessed are varied stepwise, and the results of assessment made at the significance levels are associated with contour lines. Namely, in the first embodiment of the present invention, the significance levels include levels 0.001, 0.005, 0.01, and 0.05. Active areas hypothetically detected at the significance levels are indicated with the contour lines. The results of detection shown in FIG. 4C are expressed with the contour line associated with the significance level of 0.01. If a well-known imaging program is used to display the contour lines with shades of a certain color, the active areas would be presented to a user in a well-visualized manner.

FIG. 4F shows an example of a display form in which the results of FIG. 4D comparative with FIG. 4C are presented in the easier-to-understand manner. As described previously, the conventional test of hypothesis based on the synchronousness of the amplitude of a signal cannot detect an active area at all with a significance level set to 1%. FIG. 4F shows the results of detection performed at significance levels of 2% and 5%. The number of contour lines is only two, and the display is therefore coarse-grained.

Second Embodiment

Figure 5A:
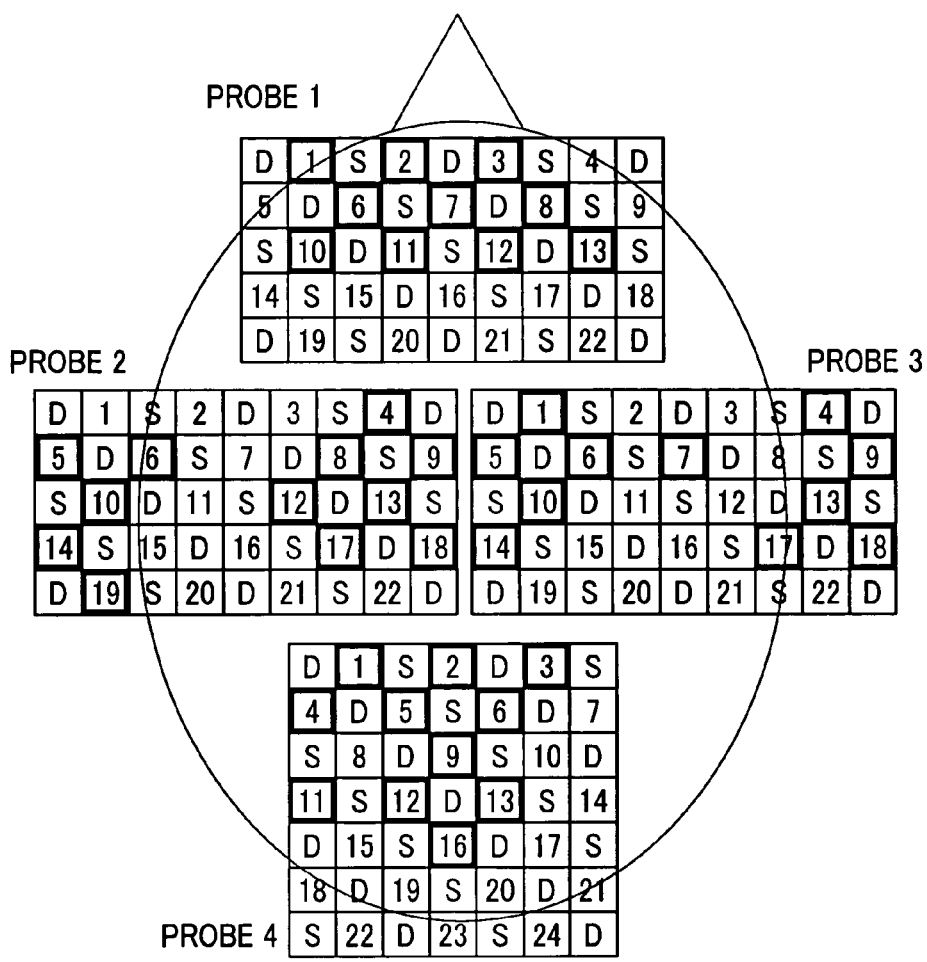
FIG. 5A illustratively shows an example of the structures of probes included in the second embodiment and the arrangement thereof.

The second embodiment is concerned with detection of an activity performed by asking an examinee to listen to the played-back commentary on a baseball game as a stimulus/task instruction sequence and to imagine standing on a field as a batter. FIG. 5A illustratively shows an example of the structures of probes employed in the second embodiment and the arrangement of the probes, and also shows the results of assessment of the synchronousness of the phase of a signal. An oval drawing expresses the head seen from above, and a triangle expresses the nose seen from above. Probes 1, 2, 3, and 4 are arranged on the frontal region of the head, the right and left temporal regions thereof, and the occipital region thereof. The probes 1, 2, and 3 are structured so that twenty-two measurement channels will be formed in each probe. The probe 4 is structured so that twenty-four measurement channels will be formed therein.

FIG. 5A illustratively shows an example of the structures of the probes employed in the second embodiment and the arrangement thereof, and shows the results of assessment of the synchronousness of the phase of a signal.

Figure 5B:
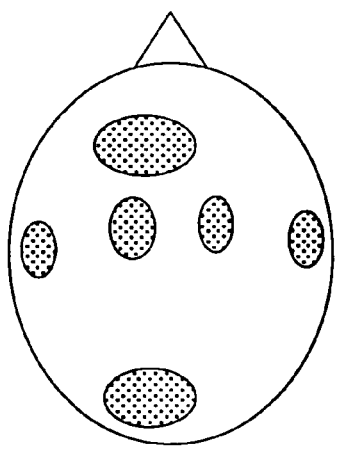
FIG. 5B shows the results shown in FIG. 5A in the form of an image expressing the head, which is visualized, seen from above similarly to the display form shown in FIG. 4E.

FIG. 5B shows, similarly to FIG. 4E, the results shown in FIG. 5A in a well-visualized manner together with a drawing expressing the head seen from above. As apparent from FIG. 5B, an activity stemming from hearing of the played-back commentary is observed in the right and left infratemporal regions (auditory fields). An activity stemming from imagination of batting is observed in the supra-occipital region (optical field). An activity stemming from preparation for modeling a motion is observed in the frontal region. An activity stemming from modeling of a motion is observed in the right and left supratemporal regions (motor fields).

In the foregoing example, an active area can be accurately detected, and a subject's brain activity can be assessed further exactly.

Third Embodiment

According to the second embodiment, a subject's brain activity is detected by adopting a played-back signal, which is heard, as a standard signal. The levels of synchronousness of the phases of signals may be assessed, and a signal which is produced in a channel and whose phase is highly synchronous with the phase of the standard signal may be adopted as a new standard signal. In this case, an active brain area can be detected further exactly.

According to the third embodiment, first, a measurement channel in which a signal which is produced responsively to hearing of a played-back signal and whose phase is highly synchronous with the phase of the played-back signal serving as a standard signal is produced is detected. FIG. 6 shows detected measurement channels in which a signal which is produced responsively to hearing of the played-back signal and whose phase is highly synchronous with the phase of the standard signal is produced. In this example, a signal that is most highly synchronous with the standard signal is produced in the channel 10 in a probe 2.

Figure 7A:
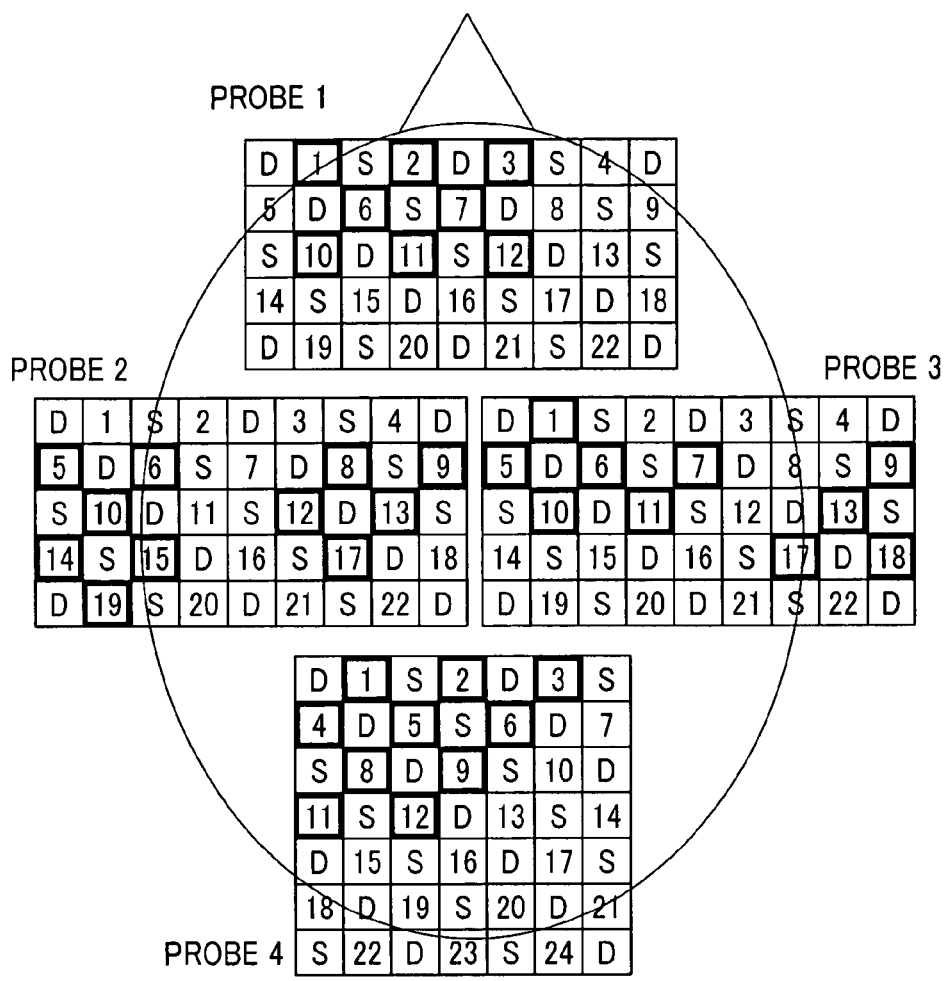
FIG. 7A and FIG. 7B shows the results of assessment of the synchronousness of the phase of a signal, which is produced responsively to hearing of a played-back signal, with the phase of the standard signal with a significance level set to 1%.
Figure 7B:
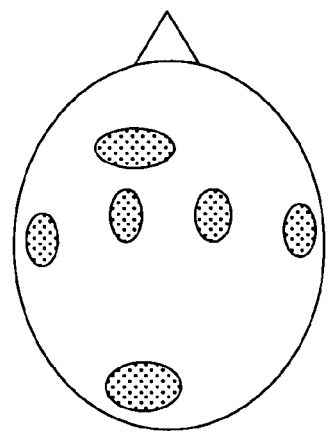

The signal in the channel 10 in the probe 2 is regarded as a new standard signal. The synchronousness of the phase of the signal produced responsively to the hearing of the played-back signal is assessed using the new standard signal. FIG. 7A and FIG. 7B show the results of assessment of the synchronousness of the phase of a signal, which is produced responsively to hearing of a played-back signal, with the standard signal, wherein the assessment is made with a significance level set to 1%. Compared with FIG. 5A, although the same results of measurement are used for assessment, since a signal in a measurement channel whose phase is highly synchronous with the standard signal that is the signal produced responsively to hearing of the played-back signal is adopted as a practical standard signal, a localized active area can be detected. When FIG. 7A is compared with FIG. 5A, the phase of a signal in the channel 13 in the probe 1 is assessed to be asynchronous with the standard signal. The phase of a signal in the channel 15 in the probe 2 is assessed to be synchronous therewith, and the phase of a signal in the channel 18 therein is assessed to be a synchronous therewith. The phases of signals in the channels 4 and 14 in the probe 3 are assessed to be asynchronous therewith, and the phase of a signal in the channel 11 therein is assessed to be synchronous therewith. The phases of signals in the channels 13 and 16 in the probe 4 are assessed to be asynchronous therewith. Consequently, visualized information shown in FIG. 7B makes it possible to recognize the activities in more limited areas than the visualized information shown in FIG. 5B.

Fourth Embodiment

A brain activity does not always take place in the whole of the brain. The brain activity in a certain area in the brain triggers a brain activity in any other area. Thus, the brain activity is known to be a time-sequential action. According to the third embodiment, a test of hypothesis was performed in order to detect the time-sequential brain activity by assessing the results of measurement performed according to the second embodiment.

Figures 2A, 2B:
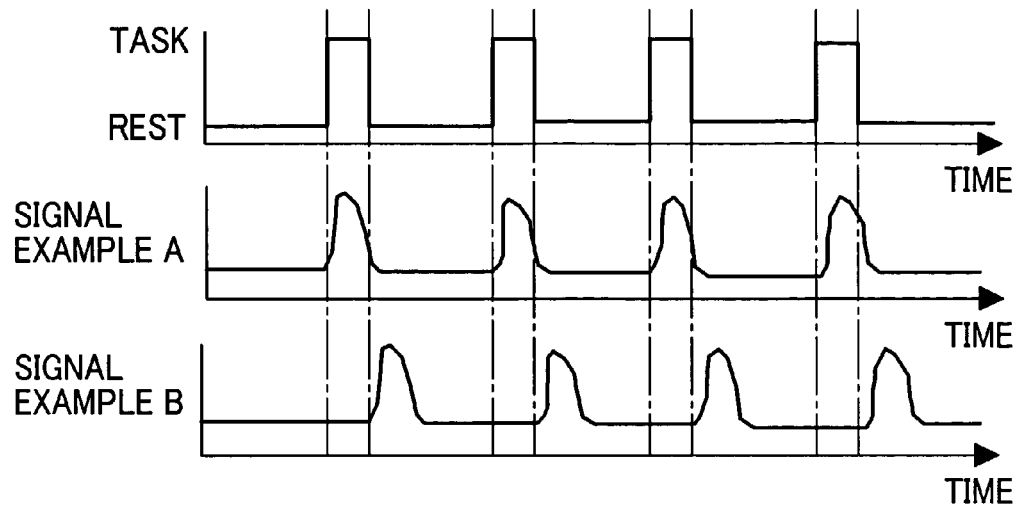
FIG. 2A and FIG. 2B are simple explanatory diagrams concerning the synchronousness of a signal with a task.
Figure 8:
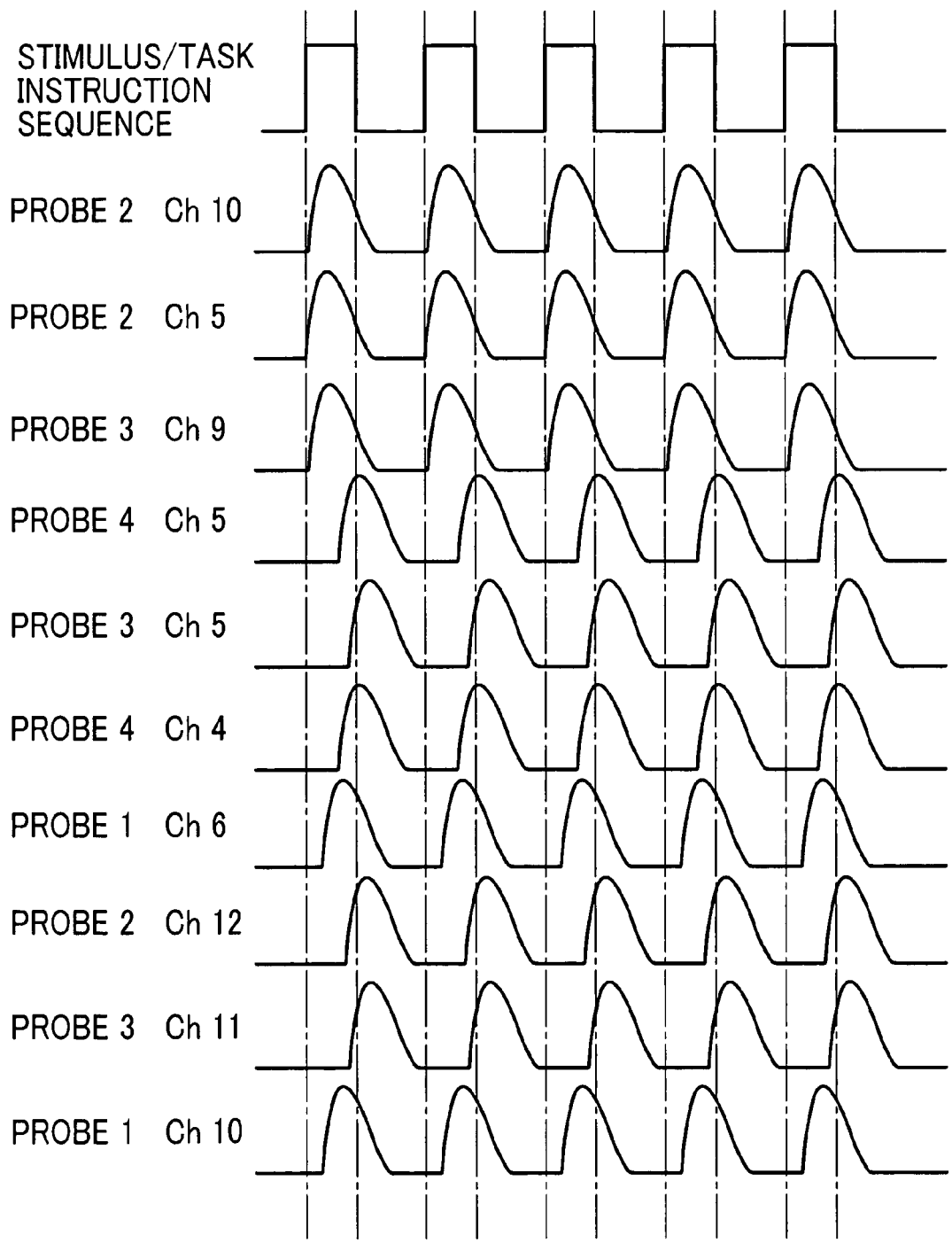
FIG. 8 shows the quickness levels of responses to signals, which are produced responsively to hearing of a played-back signal serving as a standard signal in the measurement channels shown in FIG. 6 and of which phases are highly synchronous with the phase of the signal produced.
Figure 9A:
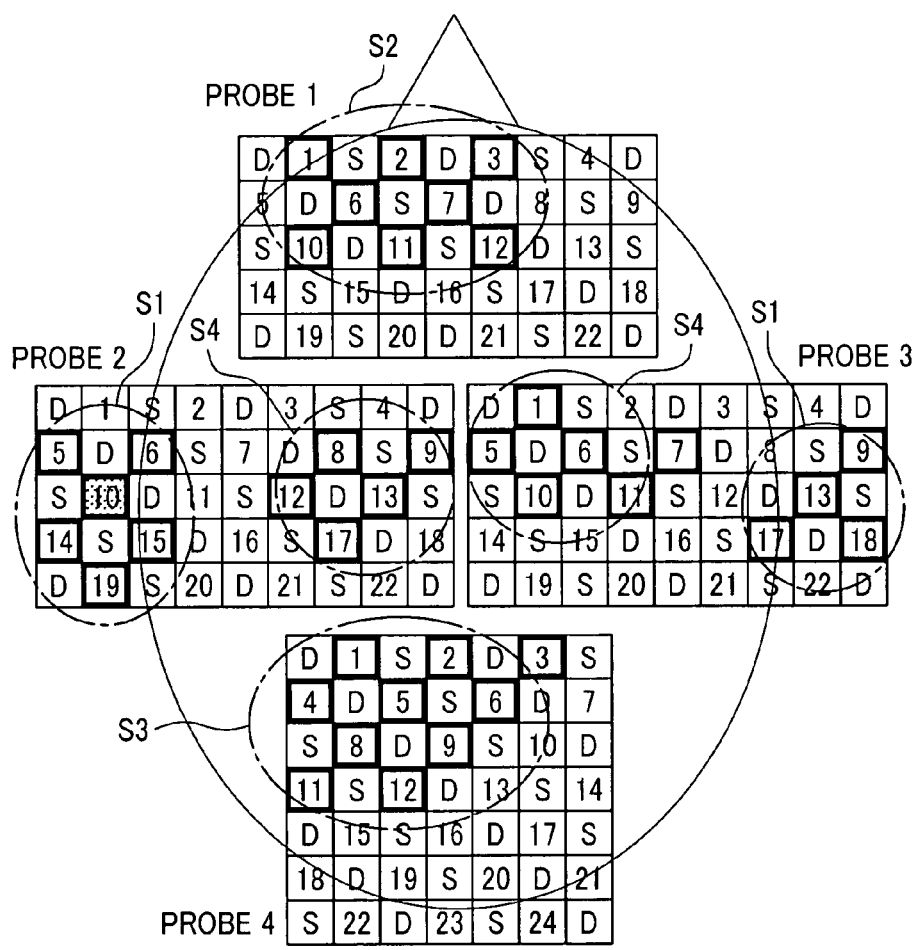
FIG. 9 shows information on the quickness levels of responses superposed on the results of assessment, which are shown in FIG. 7A, of the synchronousness of the phase of a signal, which is produced responsively to hearing of a played-back signal serving as a standard signal, with the phase of the standard signal with a significance level set to 1%.
Figure 9B:
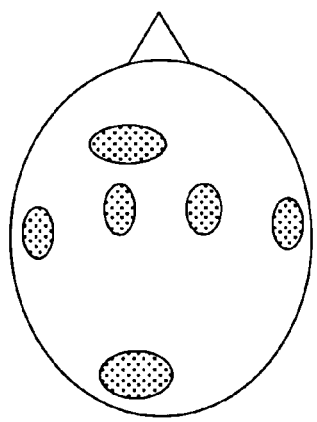

FIG. 8 shows the quickness levels of the responses made by signals, which are produced responsively to a played-back signal serving as a standard signal and of which phases are highly synchronous with that of the standard signal, in the measurement channels shown in FIG. 6 to the hearing of the played-back signal. There is difficulty in plotting the waveform of the played-back signal serving as the standard signal or a stimulus/task instruction sequence as well as the waveforms of responsive signals. The responsive signals are illustratively shown in relation to the stimulus/task instruction sequence described in conjunction with FIG. 2. The axis of abscissas indicates time, and the axis of ordinates indicates the magnitudes of signals. FIG. 9 shows the information on the quickness levels of the responses superposed on the results of assessment, which are shown in FIG. 7, of the synchronousness of the phase of a signal, which is produced responsively to hearing of a played-back signal, made with a significance level set to 1%.

Referring to FIG. 8, the signal in the channel 10 in the probe 2 is the quickest to respond. In FIG. 9, a square expressing the channel 10 in the probe 2 is filled with dots. The signals in the channel 10 in the probe 2 and in the channel 9 in the probe 3 are the next quickest to respond. Namely, the signals in the areas S1 in the probes 2 and 3 covering the channels 5 and 9 are the quickest to respond. The signals in the channels 6 and 10 in the probe 1 are the next quickest to respond. Namely, the signals in the area S2 in the probe 1 are the second quickest to respond. The signals in the channels 4 and 5 in the probe 4 are the next quickest to respond. Namely, the signals in the area S3 in the probe 4 are the third quickest to respond. Finally, the signals in the channels 5 and 11 in the probe 3 and in the channel 12 in the probe 2 are the fourth quickest to respond. Namely, the signals in the areas S4 in the probes 2 and 3 are the fourth quickest to respond.

Consequently, the activities in the right and left infratemporal regions (auditory fields) stemming from hearing of a played-back signal are detected in the area S1 in FIG. 9. The activity in the frontal region stemming from preparation for modeling a motion is then detected in the area S2 in FIG. 9. Thereafter, the activity in the supra-occipital region (optical field) stemming from imagination of batting is detected in the area S3 in FIG. 9. Finally, the activities in the right and left supratemporal regions (motor fields) stemming from modeling of a motion are detected in the areas S4 in FIG. 9.

As apparent from FIG. 8, when it says that a signal is quick to respond, it means a matter of comparison. The response time is merely on the order of several seconds. Nevertheless, when signals are divided into groups by quickness of a response, if places where the signals are detected are visibly presented to a user, the brain activities of a subject can be dynamically visualized.

Figure 10:
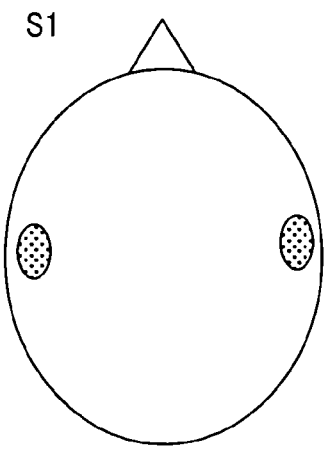
FIG. 10 shows examples of images displayed in order to dynamically visualize the brain activities of a subject.
Figure 10:
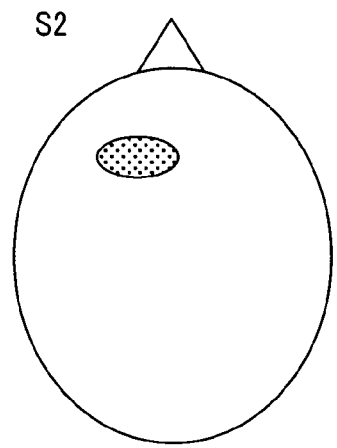
Figure 10:
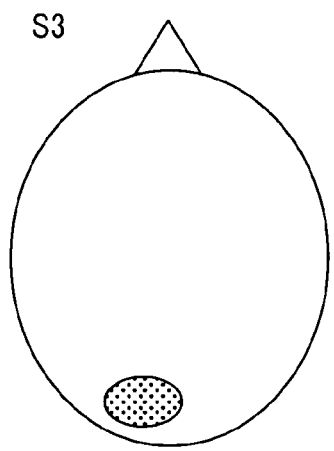
Figure 10:
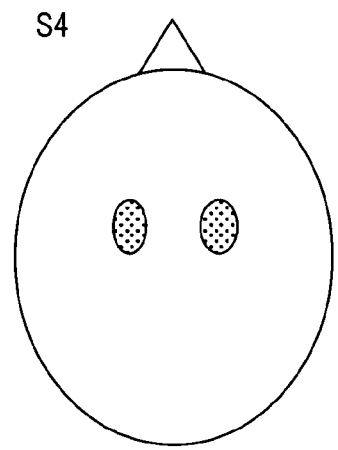
Figure 10:
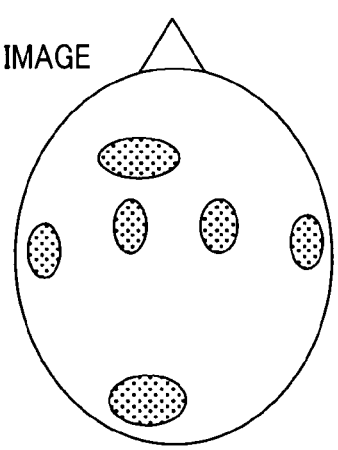

FIG. 10 shows an example of a display form in which the brain activities of a subject are dynamically visualized. An image S1 shows the areas S1 in FIG. 9 and contains dotted circles rendering the active areas in the right and left infratemporal regions (auditory fields). The area and shape of the circle are determined with the position of the measurement channel in which a signal whose phase is highly synchronous with a played-back signal is produced, and the number of circles depends on the number of measurement channels. The same applies to the subsequent description. An image S2 shows the area S2 in FIG. 9, and contains a dotted circle rendering the active area in the frontal region of which activity stems from preparation of modeling of a motion. An image S3 shows the area S3 in FIG. 9, and contains a dotted circle rendering an active area in the supra-occipital region (optical field) of which activity stems from imagination of batting. An image S4 shows the areas S4 in FIG. 9, and contains dotted circles rendering the active areas in the right and left supratemporal regions (motor fields) of which activities stem from modeling of a motion.

A whole image is produced by integrating the images S1 to S4 into one, and is identical to FIG. 7B.

If the images S1 to S4 are sequentially and orderly displayed on the display means 211 as a motion picture that makes progress as quickly as a user can see it with ease, the user would feel as if he/she saw the subject's brain active areas being switched in real time. After the images are displayed like a motion picture, the whole image may be displayed so that the overall brain activities can be assessed.

The immediateness of an activity is verified based on an average phase difference observed in each region. Namely, the smaller the phase difference is, the more immediately the activity takes place.

Fifth Embodiment

In order to discuss a time-sequential change in a brain activity using a motion picture, as described previously, a time-sequential change in a synchronous state is checked by defining a short time window (covering several hundreds of data items). A synchronization index serving as a statistical index is calculated during the period, and a synchronization index at the center time instant within the time window is adopted as a representative synchronization index. The time window is then shifted in units of a certain time in order to detect a time-sequential change in the synchronization index. Based on the time-sequential change in the synchronization index, the synchronousness of the phase of a signal, which is produced in a measurement area, with a stimulus is assessed. The results of assessment are displayed as a time-sequential change in the display form shown in, for example, FIG. 7B. According to this technique, a change in a phase difference can be sensitively grasped. The plurality of functions of the brain can be presented by accurately visualizing the time-varying relationships among the activities in the regions of the brain.

The synchronousness of the phase of a signal is independent of the amplitude thereof. Therefore, the brain activities or the functional connectivity can be presented in an appropriate manner irrespective of the human cranial structure.

The present invention will prove helpful in assessing the impairment in a brain function or in assessing the recovering state of a person whose brain function is impaired. Moreover, the present invention can be utilized for helping a patient with rehabilitation.

What is claimed is:

1. An optical measurement method comprising the steps of:
    irradiating a plurality of regions on a surface of a subject's head with light;
    detecting an amount of transmitted light in a plurality of regions separated by a predetermined distance from the incident regions;
    applying a predefined stimulus/task instruction sequence to a subject;
    using the stimulus/task instruction sequence as a reference phase signal to calculate a synchronization index indicating the synchronousness of the phase of a signal, which represents a detected amount of transmitted light, with the reference phase signal;
    adopting as a second reference phase signal a signal which represents an amount of transmitted light and whose phase is found based on a synchronization index, which indicates the synchronousness of the phase of the signal, to be most highly synchronous with the reference phase signal;
    calculating a synchronization index indicating the synchronousness of the phase of a signal, which represents a detected amount of transmitted light, with the phase of the second reference phase signal; and
    outputting to a display only a signal, which represents a detected amount of transmitted light and of which the synchronization index indicating the synchronousness of the phase thereof with the phase of the second reference phase signal is equal to or larger than a predetermined threshold, as a measured value indicating a brain activity of the subject.

2. An optical measurement system comprising:
    means for irradiating a plurality of regions on a surface of a subject's head with light;
    means for detecting an amount of transmitted light in a plurality of regions separated by a predetermined distance from the incident regions;
    means for applying a predefined stimulus/task instruction sequence to a subject;
    means for using the stimulus/task instruction sequence as a reference phase signal to calculate a synchronization index indicating synchronousness of the phase of a signal, which represents a detected amount of transmitted light, with the phase of the reference phase signal, and transmitting a signal, which represents a detected amount of transmitted light and of which the synchronization index indicating the synchronousness of the phase thereof is equal to or larger than a predetermined threshold, as a measured value indicating a brain activity of the subject; and
    means for displaying an output of the transmitting means.

3. The optical measurement system according to claim 2, wherein the means for transmitting a signal as a measured value indicating a brain activity serves as means for: using the stimulus/task instruction sequence as the reference phase signal to calculate a synchronization index indicating the synchronousness of the phase of a signal, which represents a detected amount of transmitted light, with the phase of the reference phase signal; adopting as a second reference phase signal a signal which represents an amount of transmitted light and whose phase is found based on a synchronization index, which indicates the synchronousness of the phase of the signal, to be most highly synchronous with the reference phase signal; calculating a synchronization index indicating the synchronousness of the phase of a signal, which represents a detected amount of transmitted light, with the phase of the second reference phase signal; and adopting only a signal, which represents a detected amount of transmitted light and of which the synchronization index indicating the synchronousness of the phase thereof with the phase of the second reference phase signal is equal to or larger than a predetermined threshold, as a measured value indicating a brain activity of the subject.

4. An optical measurement system comprising:
    a means for irradiating a plurality of regions on a surface of a subject's head with light;
    a means for detecting an amount of transmitted light in a plurality of regions separated by a predetermined distance from the incident regions;
    a means for applying a predefined stimulus/task instruction sequence to a subject; and
    a means for using the stimulus/task instruction sequence as a reference phase signal to calculate a synchronization index indicating the synchronousness of the phase of a signal, which represents a detected amount of transmitted light, with the phase of the reference phase signal, transmitting only a signal, which represents a detected amount of transmitted light and of which the synchronization index indicating the synchronousness of the phase thereof is equal to or larger than a predetermined threshold, as a measured value indicating a brain activity of the subject, and visualizing the signal, which represents the measured value, by displaying an image at a position in an image, which expresses the subject's head, associated with the measured position.

5. The optical measurement system according to claim 4, wherein the image displayed at the position associated with the measured position contains a plurality of contour lines associated with threshold values of the predetermined threshold to be used to verify a synchronization index indicating the synchronousness of the phase of a signal.

6. The optical measurement system according to claim 4, wherein the image displayed at the position associated with the measured position is displayed as an image contained in a motion picture that comprises images which express measured positions divided into groups according to quickness of a response made to the stimulus/task instruction sequence and which are switched based on quickness levels of responses.

7. The optical measurement system according to claim 4, wherein: the synchronization index indicating synchronousness of the phase of a signal is a synchronization index indicating the synchronousness of the phase of a signal produced within a short time window; the synchronousness of the phase of a signal produced in a measured area is assessed based on a synchronization index that indicates the synchronousness of the phase of a signal and that is calculated by shifting the time window in units of a certain time; measured positions are visualized according to values of a predetermined threshold to be used to verify a synchronization index indicating the synchronousness of the phase of a signal produced within each time window; and time-sequential changes in the measured positions are displayed according to the values of the predetermined threshold.

* * * * *